US010722550B2

(12) United States Patent
Engelthaler et al.

(10) Patent No.: US 10,722,550 B2
(45) Date of Patent: Jul. 28, 2020

(54) COMPOSITIONS AND METHODS FOR THE TREATMENT OF FUNGAL INFECTIONS

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(72) Inventors: David Engelthaler, Flagstaff, AZ (US); Elizabeth Driebe, Flagstaff, AZ (US); Hongwei "Holly" Yin, Phoenix, AZ (US); Michael Valentine, Flagstaff, AZ (US); Donald Chow, Phoenix, AZ (US); Jolene Bowers, Flagstaff, AZ (US); Paul Keim, Flagstaff, AZ (US); Bridget Barker, Flagstaff, AZ (US)

(73) Assignees: The Translational Genomics Research Institute, Phoenix, AZ (US); Arizona Board of Regents on behalf of Northern Arizona University, Flagstaff, AZ (US)

( * ) Notice: Subject to any disclaimer, the term of this patent is extended or adjusted under 35 U.S.C. 154(b) by 0 days.

(21) Appl. No.: 16/250,612

(22) Filed: Jan. 17, 2019

(65) Prior Publication Data

US 2019/0151405 A1 May 23, 2019

Related U.S. Application Data

(63) Continuation of application No. 14/949,965, filed on Nov. 24, 2015, now Pat. No. 10,213,478.

(Continued)

(51) Int. Cl.
*A61K 31/41* (2006.01)
*A61K 31/135* (2006.01)
(Continued)

(52) U.S. Cl.
CPC ............ *A61K 38/13* (2013.01); *A61K 31/138* (2013.01); *A61K 31/277* (2013.01);
(Continued)

(58) Field of Classification Search
CPC . A61K 31/4196; A61K 31/183; A61K 31/138
(Continued)

(56) References Cited

U.S. PATENT DOCUMENTS 4,782,059 A 11/1988 Gadebusch et al.
8,722,335 B2 5/2014 Liu et al.
(Continued)

OTHER PUBLICATIONS

Tosh et al. "The incidence of Coccidioidomycosis in San Luis Obispo, Califonia," Poster Abstracts/American Journal of Infection Control 40 (2012) e173, Present No. 16-240 (Year: 2012).*
(Continued)

*Primary Examiner* — Shengjun Wang
(74) *Attorney, Agent, or Firm* — Rodney J. Fuller; Booth Udall Fuller, PLC

(57) ABSTRACT

The present invention comprises methods of treating an infection using a pharmaceutical composition comprising an active ingredient selected from Table 1. In some aspects, the infection can be caused by one or more pathogens, including fungal pathogens. For example, the infection may be Valley Fever.

20 Claims, 12 Drawing Sheets

| Cocci-LOPAC Control | | 0hr | 24hr | 48hr | 72hr | 96hr | 120hr |
|---|---|---|---|---|---|---|---|
| Blank | Avg OD600 | 0.0436 | 0.0381 | 0.0383 | 0.0385 | 0.0389 | 0.0394 |
| | %CV | 22.4% | 9.1% | 8.5% | 9.1% | 8.5% | 8.9% |
| Upper Plate Culture | Avg OD600 | 0.0420 | 0.0440 | 0.1256 | 0.3230 | 0.3974 | 0.4901 |
| | %CV | 3.0% | 3.3% | 8.8% | 6.2% | 4.3% | 6.1% |
| | OD600/Blank | 1.0 | 1.2 | [illegible] | 8.4 | 10.2 | 12.4 |
| | Z Factor | -23.4653 | -1.4370 | 0.5104 | 0.7513 | 0.8303 | 0.7781 |
| Lower Plate Culture | Avg OD600 | 0.0421 | 0.0437 | 0.1378 | 0.3408 | 0.4072 | 0.5026 |
| | %CV | 3.6% | 5.8% | [illegible] | 6.8% | 5.4% | 6.1% |
| | OD600/Blank | 1.0 | 1.1 | 3.6 | 8.8 | 10.5 | 12.7 |
| | Z Factor | -26.4470 | -2.1382 | [illegible] | 0.7351 | 0.7929 | 0.7798 |

Related U.S. Application Data

(60) Provisional application No. 62/083,429, filed on Nov. 24, 2014.

(51) Int. Cl.

| | |
|---|---|
| ***A61K 38/13*** | (2006.01) |
| ***A61K 31/7135*** | (2006.01) |
| ***A61K 31/58*** | (2006.01) |
| ***A61K 31/5377*** | (2006.01) |
| ***A61K 31/5415*** | (2006.01) |
| ***A61K 31/4196*** | (2006.01) |
| ***A61K 31/496*** | (2006.01) |
| ***A61K 31/495*** | (2006.01) |
| ***A61K 45/06*** | (2006.01) |
| ***A61K 31/138*** | (2006.01) |
| ***A61K 31/277*** | (2006.01) |
| ***A61K 31/353*** | (2006.01) |
| ***A61K 31/404*** | (2006.01) |
| ***A61K 31/4174*** | (2006.01) |
| ***A61K 31/428*** | (2006.01) |
| ***A61K 31/4741*** | (2006.01) |
| ***A61K 31/609*** | (2006.01) |

(52) U.S. Cl.

CPC .......... *A61K 31/353* (2013.01); *A61K 31/404* (2013.01); *A61K 31/4174* (2013.01); *A61K 31/4196* (2013.01); *A61K 31/428* (2013.01); *A61K 31/4741* (2013.01); *A61K 31/495* (2013.01); *A61K 31/496* (2013.01); *A61K 31/5377* (2013.01); *A61K 31/5415* (2013.01); *A61K 31/58* (2013.01); *A61K 31/609* (2013.01); *A61K 31/7135* (2013.01); *A61K 45/06* (2013.01)

(58) Field of Classification Search

USPC .......................................... 514/383, 648, 646

See application file for complete search history.

(56) References Cited

U.S. PATENT DOCUMENTS

| | | | |
|---|---|---|---|
| 2006/0194769 | A1 | 8/2006 | Johnson et al. |
| 2013/0243886 | A1 | 9/2013 | Hu et al. |

OTHER PUBLICATIONS

Higgins et al. "Treatment of Coccidioides immitis pneumonia in two horse with fluconazole," Veterinary Record, 2006, vol. 159, pp. 349-351 (Year: 2006).*

Kolaczkowski, M., et al. Phenothiazines as potent modulator of yeast multidrug resistance. International Journal of Antimicrobial Agents, 2003; 22(3):279-283.

Butts, A., et al. A repurposing approach identifies off-patent drugs with fungicidal Cryptococcal activity, a common structural chemotype, and pharmacological properties relevant to the treatment of *Cryptococcosis*. Eukaryotic Cell, 2013; 12(2):278-287.

Drutz, D. J., et al. Human sex hormones stimulate the growth and maturation of Coccidiodes immitis. Infection and Immunity, 1981; 32(2):897-907.

Trump, D. L., et al. High-Dose tamoxifen, a potential multidrug-resistance-reversal agent: Phase 1 trial in combination with vinblastine. Journal of the National Cancer Institute, 1992; 84(23):1811-1816.

Graybill, J. R., et al. Treatment of Coccidioidomycosis with Ketoconazole: Clinical and Laboratory Studies of 18 Patients. Reviews of Infectious Diseases, 1980; 2(4):661-673.

Valentine, M., et al. Establishing a Low-Cost, High-Throughput Screening Assay for Compounds Efficacious Against the Fungus *Coccidioides*, the Causative Agent of Valley Fever. Poster presented at Cocci Study Group 58th Annual Meeting (Phoenix, Arizona) on Apr. 5, 2014.

* cited by examiner

| Cocci-LOPAC Control | | 0hr | 24hr | 48hr | 72hr | 96hr | 120hr |
|---|---|---|---|---|---|---|---|
| Blank | Avg OD600 | 0.0436 | 0.0381 | 0.0383 | 0.0385 | 0.0389 | 0.0394 |
| | %CV | 22.4% | 9.1% | 8.5% | 9.1% | 8.5% | 8.9% |
| Upper Plate Culture | Avg OD600 | 0.0420 | 0.0440 | 0.1256 | 0.3230 | 0.3974 | 0.4901 |
| | %CV | 3.0% | 3.3% | 8.8% | 6.2% | 4.3% | 6.1% |
| | OD600/Blank | 1.0 | 1.2 | 3.3 | 8.4 | 10.2 | 12.4 |
| | Z Factor | -23.9653 | -1.4370 | 0.5104 | 0.7513 | 0.8300 | 0.7781 |
| Lower Plate Culture | Avg OD600 | 0.0421 | 0.0437 | 0.1378 | 0.3408 | 0.4072 | 0.5026 |
| | %CV | 3.6% | 5.8% | 12.9% | 6.8% | 5.4% | 6.1% |
| | OD600/Blank | 1.0 | 1.1 | 3.6 | 8.8 | 10.5 | 12.7 |
| | Z Factor | -26.4470 | -2.1382 | 0.3694 | 0.7351 | 0.7929 | 0.7799 |

| Cocci-LOPAC Control | | 0hr | 24hr | 48hr | 72hr | 96hr | 120hr |
|---|---|---|---|---|---|---|---|
| Blank | Avg OD600 | 0.0322 | 0.0314 | 0.0334 | 0.0321 | 0.0348 | 0.0355 |
| | %CV | 3.3% | 2.0% | 2.9% | 2.4% | 7.6% | 9.8% |
| Cocci Culture | Avg OD600 | 0.0386 | 0.0405 | 0.1326 | 0.2155 | 0.2932 | 0.3803 |
| | %CV | 2.5% | 4.5% | 8.8% | 5.6% | 6.1% | 7.6% |
| | OD600/Blank | 1.2 | 1.3 | 3.8 | 6.5 | 8.2 | 10.5 |
| | Z Factor | 0.0387 | 0.1735 | 0.6263 | 0.7913 | 0.7741 | 0.7316 |

| | | IC50 Value [uM] | | | | | |
|---|---|---|---|---|---|---|---|
| | | 48hr | 72hr | 96hr | 120hr | 144hr | 168hr |
| Clotrimazole | Run#1 | 0.070 | 0.096 | 0.102 | 0.087 | 0.065 | 0.069 |
| | Run#2 | 0.037 | 0.032 | 0.059 | 0.048 | 0.050 | 0.065 |
| Dequalinium Chloride Hydrate | Run#1 | 1.438 | 1.347 | 1.618 | 1.687 | 1.535 | 1.611 |
| | Run#2 | 0.836 | 0.873 | 0.962 | 0.936 | 0.956 | 0.977 |
| Thioridazine hydrochloride | Run#1 | 23.570 | 21.860 | 15.030 | 12.960 | 10.590 | 11.240 |
| | Run#2 | 29.670 | 17.360 | 17.790 | 16.790 | 16.160 | 15.950 |
| Ketoconazole | Run#1 | 0.078 | 0.108 | 0.109 | 0.149 | 0.066 | 0.070 |
| | Run#2 | 0.042 | 0.034 | 0.077 | 0.065 | 0.047 | 0.077 |
| Trifluoperazine dihydrochlorid | Run#1 | 18.290 | 20.110 | 14.430 | 12.720 | 11.320 | 12.020 |
| | Run#2 | 27.370 | 19.870 | 20.620 | 17.010 | 16.300 | 16.230 |
| Fluphenazine dihydrochloride | Run#1 | 23.810 | 23.300 | 17.450 | 16.430 | 14.500 | 14.130 |
| | Run#2 | 28.460 | 20.640 | 24.170 | 19.570 | 16.420 | 16.670 |
| Ruthenium Red | Run#1 | >50 | >50 | >50 | >50 | >50 | >50 |
| | Run#2 | >50 | >50 | >50 | >50 | >50 | >50 |
| Niclosamide | Run#1 | 0.817 | 1.258 | 1.593 | 2.049 | 1.549 | 1.546 |
| | Run#2 | 0.235 | 0.349 | 0.771 | 0.611 | 0.627 | 0.759 |
| Tamoxifen | Run#1 | 3.079 | 3.598 | 2.397 | 2.377 | 1.348 | 1.004 |
| | Run#2 | 1.430 | 0.880 | 1.853 | 1.606 | 1.079 | 1.348 |
| Tamoxifen citrate salt | Run#1 | 2.820 | 3.502 | 2.337 | 2.306 | 1.378 | 0.991 |
| | Run#2 | 1.091 | 0.773 | 1.771 | 1.495 | 1.075 | 1.347 |
| Pentamidine isethionate salt | Run#1 | 39.340 | 39.650 | 27.660 | 32.480 | 20.240 | 17.660 |
| | Run#2 | 42.880 | 38.630 | 45.440 | 38.240 | 31.030 | 40.580 |
| GBR 12909 dihydrochloride | Run#1 | 22.420 | 22.050 | 14.580 | 12.240 | 7.184 | 6.229 |
| | Run#2 | 14.930 | 9.769 | 12.360 | 9.728 | 7.057 | 9.232 |
| Octoclothepin maleate salt | Run#1 | 27.720 | 26.450 | 15.480 | 14.070 | 11.380 | 11.300 |
| | Run#2 | 30.530 | 18.080 | 21.550 | 18.680 | 14.990 | 16.210 |
| ZM 39923 | Run#1 | 8.406 | 20.340 | 24.610 | 28.460 | 23.630 | 25.990 |
| | Run#2 | 3.006 | 4.468 | 8.575 | 7.512 | 7.784 | 12.520 |
| Cyclosporin A | Run#1 | 1.482 | 1.841 | 0.977 | 1.748 | 0.743 | 0.725 |
| | Run#2 | 0.992 | 1.231 | 0.633 | 1.007 | 0.544 | 0.511 |

FIG. 10

| | | IC50 Value [uM] | | | | | |
|---|---|---|---|---|---|---|---|
| | | 48hr | 72hr | 96hr | 120hr | 144hr | 168hr |
| Calcium Ionophore A23187 | Run#1 | 4.146 | 4.440 | 12.910 | 10.980 | 8.004 | 8.210 |
| | Run#2 | 2.787 | 2.273 | 4.002 | 4.308 | 5.193 | 5.261 |
| Beta Lapachone | Run#1 | 2.034 | 2.250 | 3.008 | 2.712 | 3.009 | 3.171 |
| | Run#2 | 1.763 | 1.606 | 2.702 | 2.371 | 2.393 | 2.891 |
| Voriconazole | Run#1 | 0.792 | 0.113 | 0.130 | 0.114 | 0.083 | 0.083 |
| | Run#2 | 0.116 | 0.094 | 0.140 | 0.122 | 0.071 | 0.094 |
| Sanguinarine chloride hydrate | Run#1 | 3.762 | 6.369 | 5.944 | 6.316 | 5.510 | 5.104 |
| | Run#2 | 8.126 | 4.997 | 5.781 | 7.068 | 5.115 | 5.853 |
| PD-166285 hydrate | Run#1 | >50 | >50 | >50 | 29.460 | 11.960 | 8.225 |
| | Run#2 | >50 | >50 | >50 | 47.370 | 21.970 | 18.760 |
| Eliprodil | Run#1 | >50 | >50 | >50 | 26.870 | 11.440 | 10.740 |
| | Run#2 | >50 | >50 | >50 | 27.450 | 13.280 | 16.880 |
| U73343 | Run#1 | >50 | >50 | >50 | >50 | >50 | >50 |
| | Run#2 | >50 | >50 | >50 | >50 | >50 | >50 |
| AS 604850 | Run#1 | 6.927 | 7.625 | 7.014 | 6.036 | 3.967 | 4.120 |
| | Run#2 | 4.472 | 2.602 | 5.219 | 4.863 | 3.460 | 4.405 |
| Indirubin-3'-oxime | Run#1 | >50 | >50 | >50 | >50 | 31.750 | 16.650 |
| | Run#2 | >50 | >50 | >50 | >50 | 15.270 | 20.410 |
| Tyrphostin AG 879 | Run#1 | 4.702 | 8.225 | 15.200 | 30.830 | 16.710 | 15.190 |
| | Run#2 | 3.388 | 3.245 | 7.455 | 8.167 | 6.946 | 9.802 |
| TBBz | Run#1 | 4.374 | 10.270 | 8.067 | 8.501 | 5.333 | 4.937 |
| | Run#2 | 7.440 | 3.979 | 5.426 | 6.302 | 4.384 | 5.046 |
| SR 59230A | Run#1 | >50 | 44.300 | 29.070 | 25.880 | 17.750 | 14.820 |
| | Run#2 | >50 | 37.830 | 31.720 | 24.160 | 14.680 | 15.400 |
| SU 5416 | Run#1 | >50 | 0.416 | 3.107 | 2.688 | 2.011 | 1.974 |
| | Run#2 | >50 | 1.022 | 2.465 | 0.744 | 1.206 | 2.522 |
| Artemether | Run#1 | >50 | 1.473 | 15.420 | 19.900 | 19.580 | 11.920 |
| | Run#2 | >50 | 4.112 | 11.760 | 11.020 | 6.279 | 15.380 |
| LP 12 hydrochloride hydrate | Run#1 | 7.127 | 20.550 | 15.480 | 14.830 | 9.261 | 7.671 |
| | Run#2 | 20.090 | 16.780 | 17.550 | 18.950 | 10.120 | 12.680 |

FIG. 10
Continued

| | | IC50 Value [uM] | | | | | |
|---|---|---|---|---|---|---|---|
| | | 48hr | 72hr | 96hr | 120hr | 144hr | 168hr |
| CGP 57380 | Run#1 | >50 | >50 | >50 | >50 | >50 | >50 |
| | Run#2 | >50 | >50 | >50 | >50 | >50 | >50 |
| Auranofin | Run#1 | 3.154 | 3.849 | 4.615 | 5.434 | 4.304 | 4.615 |
| | Run#2 | 1.517 | 1.715 | 3.114 | 2.799 | 3.227 | 3.973 |
| Indatraline hydrochloride | Run#1 | 23.650 | 19.320 | 14.740 | 12.950 | 11.190 | 12.240 |
| | Run#2 | 38.630 | 20.920 | 22.770 | 20.870 | 14.780 | 15.400 |
| Bay 11-7085 | Run#1 | 1.774 | 2.476 | 4.186 | 6.561 | 5.130 | 5.543 |
| | Run#2 | 0.365 | 0.524 | 0.986 | 1.029 | 1.284 | 1.638 |
| BIO | Run#1 | 5.453 | 7.281 | 17.830 | 22.550 | 14.420 | 17.020 |
| | Run#2 | 2.778 | 3.714 | 13.610 | 16.730 | 10.750 | 19.100 |
| Sertraline hydrochloride | Run#1 | 24.050 | 20.510 | 15.560 | 16.760 | 12.380 | 14.810 |
| | Run#2 | 26.420 | 23.490 | 32.090 | 26.980 | 19.850 | 25.210 |
| Chelerythrine chloride | Run#1 | >50 | >50 | >50 | >50 | >50 | >50 |
| | Run#2 | >50 | >50 | >50 | >50 | >50 | >50 |
| GBR 12935 dihydrochloride | Run#1 | 33.600 | 29.390 | 19.150 | 17.790 | 9.846 | 9.188 |
| | Run#2 | 26.720 | 21.560 | 22.650 | 23.530 | 9.005 | 11.210 |
| AC 93253 iodide | Run#1 | 3.663 | 5.015 | 4.801 | 5.300 | 3.774 | 3.515 |
| | Run#2 | 1.635 | 1.877 | 4.081 | 4.608 | 3.298 | 4.435 |
| Calmidazolium Chloride | Run#1 | 9.033 | 6.817 | 6.864 | 7.999 | 6.043 | 5.733 |
| | Run#2 | 4.045 | 4.439 | 4.602 | 4.369 | 4.358 | 4.354 |
| IMS2186 | Run#1 | >50 | >50 | >50 | >50 | >50 | >50 |
| | Run#2 | >50 | >50 | >50 | >50 | >50 | >50 |
| Nocodazole | Run#1 | >50 | 2.284 | 1.108 | 1.505 | 0.802 | 0.784 |
| | Run#2 | >50 | 0.951 | 0.930 | 0.788 | 0.530 | 0.519 |
| PD-173952 | Run#1 | >50 | >50 | 25.240 | 22.520 | 4.124 | 3.398 |
| | Run#2 | >50 | >50 | 22.140 | 20.190 | 3.579 | 6.756 |
| Tyrphostin A9 | Run#1 | 0.840 | 1.136 | 1.555 | 2.480 | 1.912 | 2.508 |
| | Run#2 | 0.198 | 0.302 | 1.066 | 1.135 | 1.035 | 2.129 |
| Stattic | Run#1 | 3.742 | 4.391 | 5.410 | 6.797 | 6.422 | 6.181 |
| | Run#2 | 2.392 | 2.059 | 4.054 | 4.439 | 4.803 | 6.365 |
| Methiothepin mesylate salt | Run#1 | 25.400 | 21.070 | 14.800 | 12.900 | 10.850 | 11.890 |
| | Run#2 | 29.520 | 20.840 | 22.770 | 22.200 | 15.100 | 16.250 |

FIG. 10
Continued

COMPOSITIONS AND METHODS FOR THE TREATMENT OF FUNGAL INFECTIONS

CROSS REFERENCE TO RELATED APPLICATIONS

This application is a continuation of U.S. patent application Ser. No. 14/949,965, filed on Nov. 24, 2015 (published as US 20160143987), which claims the benefit of and priority of U.S. patent application Ser. No. 62/083,429, filed on Nov. 24, 2014, the contents of each of which are hereby incorporated by reference in their entireties for any purposes.

FIELD OF INVENTION

The present invention is generally related to compositions and methods of treating infectious diseases, and particularly related to compositions and methods of treating fungal infections, such as Valley Fever.

BACKGROUND OF THE INVENTION

Coccidioidomycosis is caused by infection with *Coccidioides immitis* or *Coccidioides posadasii* (collectively "*Coccidioides*"). *C. immitis* and *C. posadasii* are the fungal etiologic agents of coccidioidomycosis (Valley Fever) and are endemic to arid soils of the southwest United States, as well as parts of Mexico, and Central and South America. Primary hosts acquire *Coccidioides* via inhalation of aerosolized arthroconidia upon soil disruption. Coccidioidomycosis most commonly causes a progressive pulmonary infection in humans and other vertebrate hosts but also can disseminate to other body parts including the skin, brain, bone, and meninges. This disseminated secondary coccidioidomycosis often is severe and can result in patient death. However, in cases where infection is resolved, patients usually acquire a specific and lifelong immunity to the fungus.

Coccidioidomycosis infection rates have increased dramatically in the last decade with the State of Arizona documenting the number of reported cases per 100,000 people having increased from 20.8 in 1997 to 186.0 in 2010. Increased physician awareness and testing likely accounts for a portion of this case increase. An additional cause for this increase may be influxes of immunologically naive individuals into Arizona. A significant number of individuals from outside the *Coccidioides* endemic region migrate annually to the desert southwest and are at greater risk for developing coccidioidomycosis, even after returning to their respective homes. These infections, therefore, are likely to escape or confound diagnosis in non-endemic regions.

For individuals with Valley Fever, there are limited treatment options and scant options in drug-discovery pipelines. Moreover, the extreme costs associated with developing and receiving FDA approval for a new chemical entity for the treatment of Valley Fever is a significant deterrent for most businesses. As such, there is an ongoing need to develop treatments for Valley Fever that comprise known compounds.

SUMMARY

In one embodiment, the invention may comprise a method of treating an infection via the administration of a pharmaceutical composition comprising a compound selected from the list of compounds recited in Table 1. In some aspects, the subject could be an animal, such as a human or a companion animal (e.g., a canine). Moreover, in some embodiments, the infection could be caused by a fungus, such as *Coccidioides immitis* or *Coccidioides posadasii* (i.e., the etiological agents of Valley Fever).

Other embodiments of the invention comprise a method for treating a subject with Valley Fever, which can include the step of administering to the subject a therapeutically effective amount of a pharmaceutical composition comprising a compound selected from the compounds recited in Table 1. In some aspects, the subject could be an animal, such as a human or a companion animal (e.g., a canine). In some embodiments, the pharmaceutical composition can include one or more pharmaceutically acceptable excipients and can be administered to the subject at a dose of 0.01 mg/kg to 30 mg/kg of body weight of subject of the compound.

Some embodiments of the invention provide a method for treating a subject with an infection, which can include the step of administering to the subject a therapeutically effective amount of a pharmaceutical composition comprising an active pharmaceutical ingredient selected from the group consisting of tamoxifen, tamoxifen citrate salt, niclosamide, beta lapachone, sanguinarine chloride hydrate, SU5416, auranofin, BAY11-7085, BIO, AC93253 iodide, stattic, tyrophostin a9 and calmidazolium chloride. In some embodiments, the pharmaceutical composition can include one or more pharmaceutically acceptable excipients and can be administered to the subject at a dose of 0.01 mg/kg to 30 mg/kg of body weight of subject of the active ingredient. In some aspects, the subject could be an animal, such as a human or a companion animal (e.g., a canine). In some aspects, the infection could be caused by a fungus, such as *Coccidioides immitis* or *Coccidioides posadasii* (i.e., the etiological agents of Valley Fever).

Additional objectives, advantages and novel features will be set forth in the description which follows or will become apparent to those skilled in the art upon examination of the drawings and detailed description which follows.

BRIEF DESCRIPTION OF THE DRAWINGS

FIG. 1A depicts the OD600 values taken at 24 hour intervals from different regions of 384-well microplates. FIG. 1B depicts an analysis of the growth of *Coccidioides posadasii*, which illustrates that after 48 hours, fungal growth can be differentiated from the media-only controls.

FIG. 2A depicts the OD600 absorbance (i.e., growth) over time of *Coccidioides posadasii* that has been treated with only DMSO and media-only wells. FIG. 2B depicts growth fold induction and Z-Factor scores based on the growth data depicted in FIG. 2A.

FIG. 3A depicts the OD600 absorbance (i.e., growth) over time of *Coccidioides posadasii* that has been treated with only DMSO and media-only wells. FIG. 3B depicts growth fold induction and Z-Factor scores based on the growth data depicted in FIG. 3A.

FIG. 5A depicts the OD600 values taken at 24 hour intervals from different regions of 384-well microplates. FIG. 5B depicts an analysis of the growth of *Coccidioides posadasii*, which illustrates that after 48 hours, fungal growth can be differentiated from the media-only controls.

FIG. 6A depicts the OD600 absorbance (i.e., growth) over time of *Coccidioides posadasii* that has been treated with only DMSO and media-only wells. FIG. 6B depicts growth fold induction and Z-Factor scores based on the growth data depicted in FIG. 6A.

FIG. 7A depicts the OD600 absorbance (i.e., growth) over time of *Coccidioides posadasii* that has been treated with only DMSO and media-only wells. FIG. 7B depicts growth fold induction and Z-Factor scores based on the growth data depicted in FIG. 7A.

FIG. 10 depicts $IC_{50}$ data from *Coccidioides posadasii* that were treated with varying concentrations of the recited drugs and incubated for 168 hours.

Figures 1A, 1B:
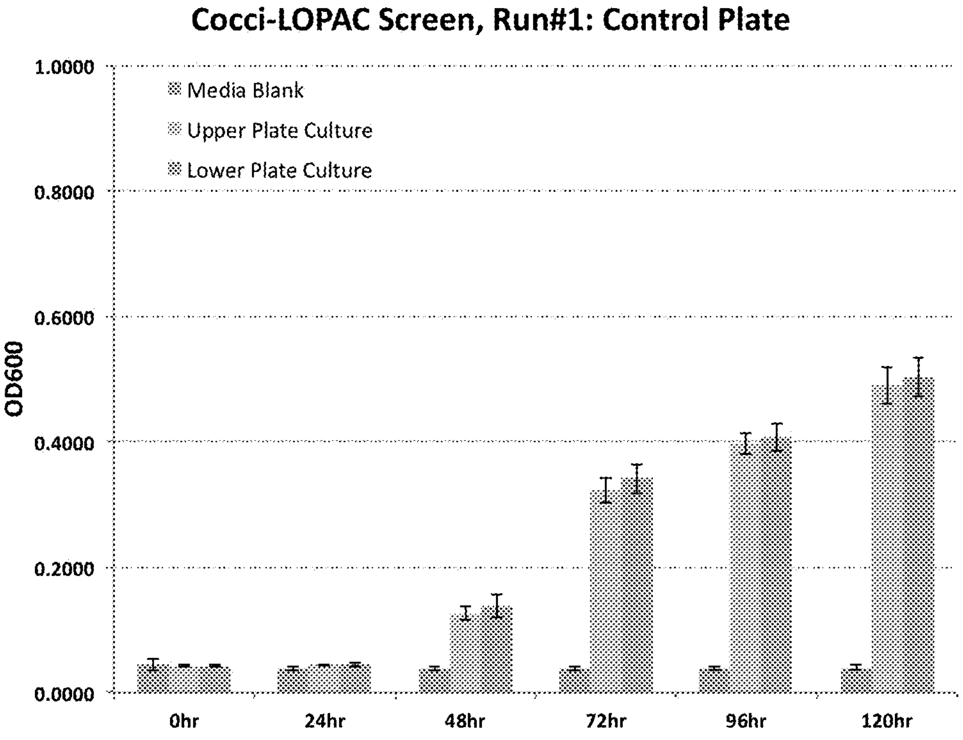
FIGS. 1A and 1B depict the results from a quality control plate illustrating the growth of *Coccidioides posadasii* over the course of a 120 hour experiment.
Figure 2A:
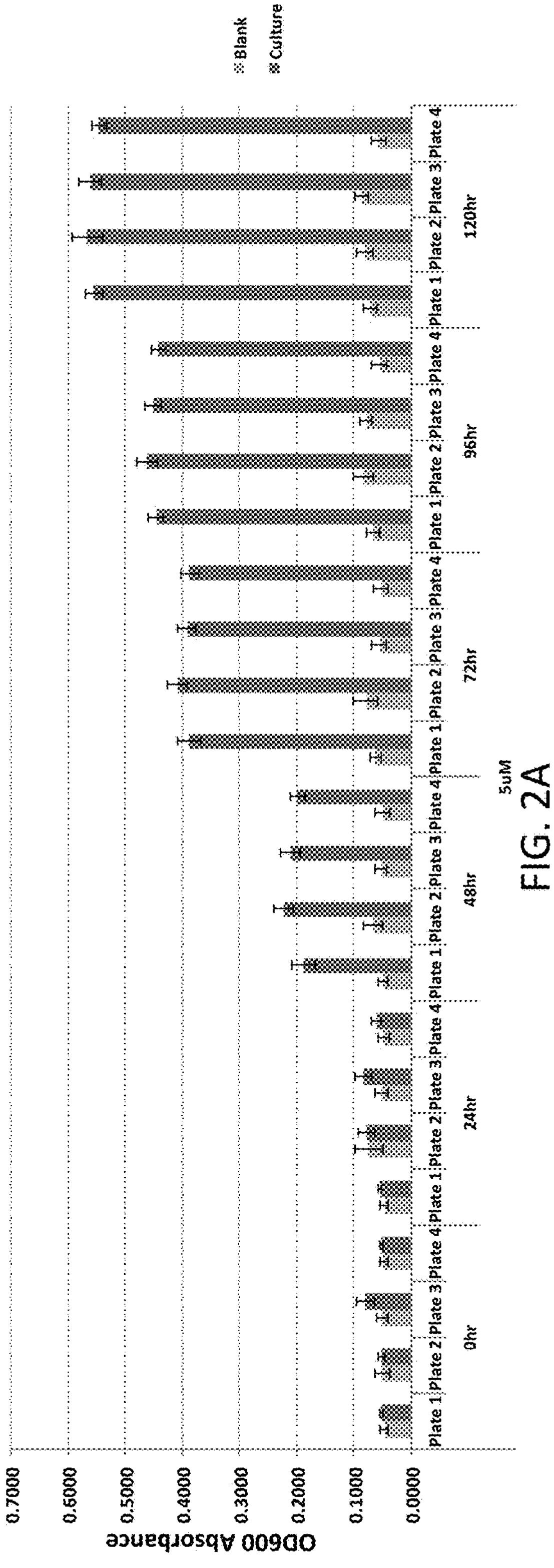
FIGS. 2A and 2B depict data from control samples from a series of microplates run with a 5 μM final concentration of compounds from the LOPAC library.
Figure 2B:
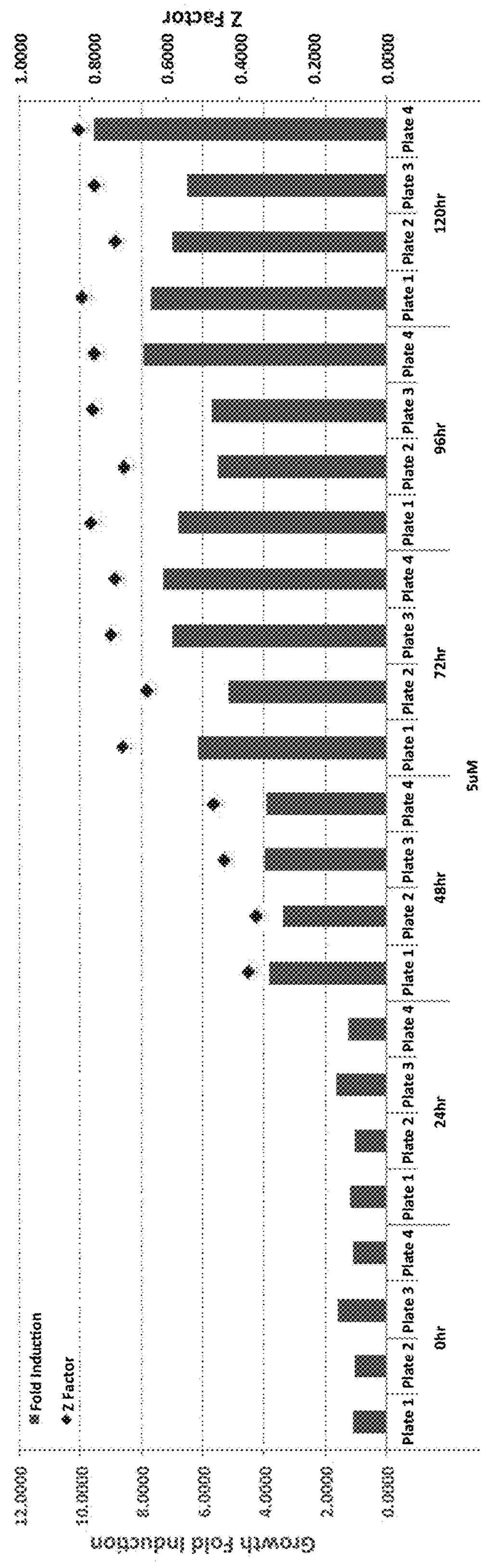
Figure 3A:
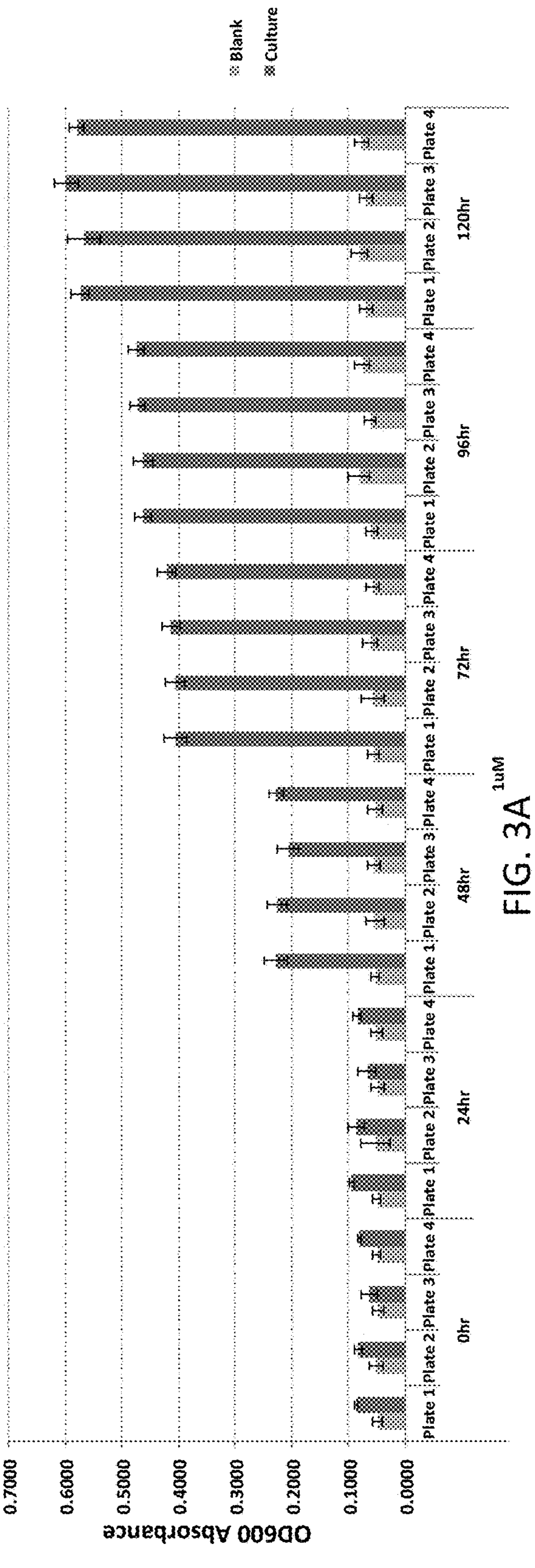
FIGS. 3A and 3B depict data from control samples from a series of microplates run with a 1 μM final concentration of compounds from the LOPAC library.
Figure 3B:
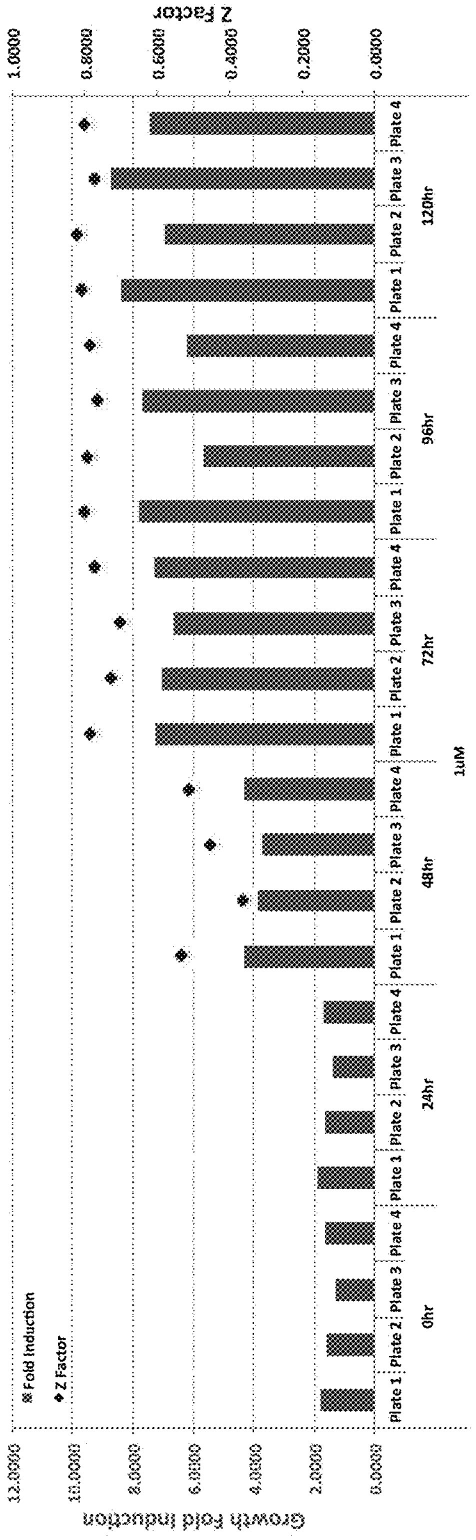

The headings used in the figures should not be interpreted to limit the scope of the claims.

DETAILED DESCRIPTION

Provided herein are compositions for treatment and methods of treating an infection caused by a microbial agent. In some aspects of the invention, the microbial agent can comprise a fungal agent (e.g., a conventional pathogen and/or an opportunistic pathogen). For example, the fungal agent can be one or more of the organisms recited in U.S. Pat. No. 8,722,335, which is incorporated by reference in its entirety for all purposes. In particular, the fungal agent may be of the genus *Coccidioides*, which is the genus known to cause coccidioidomycosis (i.e., Valley Fever).

Coccidioidomycosis is caused by infection with *Coccidioides immitis* or *Coccidioides posadasii* (collectively "*Coccidioides*"). *C. immitis* and *C. posadasii* are endemic to arid soils of the southwest United States, as well as parts of Mexico, and Central and South America. As used herein, coccidioidomycosis and Valley Fever can be used interchangeably. In some aspects, methods of treating coccidioidomycosis may comprise administration of a pharmaceutical composition to an infected subject (i.e., infected with *Coccidioides*) to halt, reduce, ameliorate, or otherwise assuage the infection (i.e., to "treat" the infection). In some embodiments, the treatment may function as a fungicidal agent (i.e., the treatment may induce death of the fungus). In other embodiments, the treatment may function as a fungistatic agent (i.e., the treatment may reduce or halt growth of the fungus).

Some embodiments of the invention may comprise the administration of a pharmaceutical composition to the subject that has been previously diagnosed with a fungal infection, such as Valley Fever. For example, in some embodiments, the subject may have been previously diagnosed with Valley Fever by one skilled in the art (e.g., a physician or a veterinarian) such that a therapeutic treatment is warranted by the diagnosis. Moreover, in other embodiments, the invention may comprise the administration of a pharmaceutical composition to a subject that may have been exposed to a *Coccidioides*-infected environment (e.g., an environment with *Coccidioides* endemic to the region/soil). As such, the administration of the pharmaceutical composition may function as a prophylactic agent to limit any potential Valley Fever infection that could occur.

In some embodiments, the pharmaceutical composition may comprise one or more of the compounds disclosed herein. The pharmaceutical composition may include one or more pharmaceutically acceptable salts of the one or more disclosed compounds, in addition to, or in lieu of the one or more disclosed compounds. In some embodiments, the disclosed compounds may be one or more known small molecules that have been previously unconnected to the treatment of infections, fungal infections, and/or coccidioidomycosis. In some aspects, at least some of the disclosed compounds may be approved by the U.S. Food and Drug Administration for the treatment of one or more indications that are unrelated to Valley Fever. For example, some of the compounds disclosed in the present application can be recognized therapeutics used to treat other conditions, such as cancer, depression, parasitic infections, arthritis, pneumonia, schizophrenia, psychosis, and other indications/conditions not related to coccidioidomycosis. In some embodiments, the one or more disclosed compounds comprise the compounds recited in Table 1. Moreover, in some embodiments, the one or more disclosed compounds can be administered to the subject in conjunction with one or more other compounds (i.e., in combination) recited in Table 1 or other compounds known to be effective against infections. For example, in some embodiments, the one or more disclosed compounds can be administered to the subject on combination with compounds that are commonly known as current standards of care for infections (e.g., Valley Fever), such as fluconazole or other anti-fungal compounds.

TABLE 1

| Compound Name |
|---|
| AC-93253 iodide |
| AS 604850 |
| Auranofin (common name - Ridaura) |
| Bay 11-7085 |
| beta-Lapachone |
| BIO |
| Calcimycin |
| Calmidazolium chloride |
| CGP 57380 |
| Chelerythrine chloride |
| Clotrimazole |
| Cyclosporin A |
| Dequalinium chloride hydrate (common name - Fluomizin) |
| Eliprodil |

TABLE 1-continued

| Compound Name |
| --- |
| GBR-12909 dihydrochloride (common name - Vanoxerine) |
| GBR-12935 dihydrochloride |
| IMS2186 |
| Indirubin-3'-oxime |
| Ketoconazole |
| Nocodazole |
| PD-166285 hydrate |
| PD173952 |
| Pentamidine isethionate (common name - Pentamidine) |
| Sanguinarine chloride |
| Sertraline hydrochloride (common names - Zoloft or Lustral) |
| SR 59230A oxalate |
| SU 5416 (common name - Semaxanib) |
| Tamoxifen |
| Tamoxifen citrate |
| Trifluoperazine dihydrochloride (common names - Eskazinyl, Eskazine, Jatroneural, Modelina, Stelazine, Terfluzine, Trifluoperaz, and Triftazin) |
| Tyrphostin A9 |
| Voriconazole |
| ZM 39923 hydrochloride |
| Artemether (common names - Rimaet or Coartem) |
| (±)-Octoclothepin maleate |
| Fluphenazine dihydrochloride |
| Thioridazine hydrochloride (common names - Riamet or Coartem) |
| Methiothepin mesylate |
| Niclosamide |
| Tyrphostin AG 879 |
| U-73343 |
| TBBz |
| Indatraline hydrochloride |
| Stattic |
| LP 12 hydrochloride hydrate |
| Ruthenium red |
| cis-(Z)-Flupenthixol dihydrochloride (common names - Depixon and Fluanxol) |

In some embodiments, the one or more disclosed compounds in Table 1 can be synthesized using conventional techniques that may be well known to those skilled in the art. In other aspects, the one or more disclosed compounds can be purchased from one or more suppliers.

The concept of a pharmaceutical composition includes one or more of the disclosed compounds or a pharmaceutically acceptable salt thereof with or without any other additive/pharmaceutically acceptable excipient. The physical form of the invention may affect the route of administration and one skilled in the art would know to choose a route of administration that takes into consideration both the physical form of the compound and the disorder to be treated. Pharmaceutical compositions that include the disclosed compounds may be prepared using methodology well known in the pharmaceutical art. A pharmaceutical composition that includes one or more of the disclosed compounds may include a second effective compound of a distinct chemical formula from the disclosed compounds. This second effective compound may have the same or a similar molecular target as the disclosed compounds or it may act upstream or downstream of the molecular target of the disclosed compounds with regard to one or more biochemical pathways.

Pharmaceutical compositions, including the one or more disclosed compounds, may include materials capable of modifying the physical form of a dosage unit (e.g., pharmaceutically acceptable excipients). In one non-limiting example, the composition includes a material that forms a coating that contains the one or more disclosed compounds. Materials that may be used in a coating include, for example, sugar, shellac, gelatin, or any other inert coating agent.

Pharmaceutical compositions including the one or more disclosed compounds may be prepared as a gas or aerosol.

Aerosols encompass a variety of systems including colloids and pressurized packages. Delivery of a composition in this form may include propulsion of a pharmaceutical composition including the one or more disclosed compounds through use of liquefied gas or other compressed gas or by a suitable pump system. Aerosols may be delivered in single phase, bi-phasic, or multi-phasic systems.

In some aspects of the invention, the pharmaceutical composition including the one or more disclosed compounds is in the form of a solvate. Such solvates are produced by the dissolution of the one or more disclosed compounds in a pharmaceutically acceptable solvent. Pharmaceutically acceptable solvents include any mixtures of one or more solvents. Such solvents may include pyridine, chloroform, propan-1-ol, ethyl oleate, ethyl lactate, ethylene oxide, water, ethanol, and any other solvent that delivers a sufficient quantity of the one or more disclosed compounds to treat the indicated condition.

Pharmaceutical compositions that include the one or more disclosed compounds may also include at least one pharmaceutically acceptable carrier/excipient. As used herein, "carrier(s)" can be used interchangeably with "excipient(s)." Carriers include any substance that may be administered with the one or more disclosed compounds with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, and oils (including petroleum, animal, vegetable or synthetic oils.) Such carriers include particulates such as a tablet or powder, liquids such as oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition, including the one or more disclosed compounds, may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers and formulations are well known in the art.

Methods of administration include, but are not limited to, oral administration and parenteral administration. Parenteral administration includes, but is not limited to intradermal, intramuscular, intraperitoneal, intravenous, subcutaneous, intrathecal, intranasal, epidural, sublingual, intramsal, intracerebral, iratraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment (e.g., areas of the respiratory tract, including the nasal cavity, the trachea, the lungs, the bronchi, etc.). Examples include local infusion during surgery; topical application, by local injection; by a catheter; by a suppository; or by an implant. Administration may be by direct injection into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include the use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle. Additional examples of suitable modes of administration are well known in the art.

A pharmaceutical composition formulated to be administered by injection may be prepared by dissolving the one or more disclosed compounds with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions including the one or more disclosed compounds may be prepared in a form that facilitates topical or transdermal administration. Such preparations may be in the form of a solution, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Determination of an effective amount of the one or more disclosed compounds is within the capability of those skilled in the art, especially in light of the detailed disclosure provided herein. The effective amount of a pharmaceutical composition used to affect a particular purpose as well as its toxicity, excretion, and overall tolerance may be determined in vitro, or in vivo, by pharmaceutical and toxicological procedures either known now by those skilled in the art or by any similar method yet to be disclosed. One example is the in vitro determination of the $IC_{50}$ (half maximal inhibitory concentration) of the pharmaceutical composition in cell lines or target molecules. Another example is the in vivo determination of the $LD_{50}$ (lethal dose causing death in 50% of the tested animals) of the pharmaceutical composition. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for administration also includes the determination of an effective therapeutic amount and a pharmaceutically acceptable dose, including the formulation of an effective dose range for use in vivo, including in humans.

Treatment of a condition, such as treatment of a subject with Valley Fever, is the practice of any method, process, or procedure with the intent of halting, inhibiting, slowing or reversing the progression of a disease, disorder, infection, or condition, substantially ameliorating clinical symptoms of a disease, disorder, infection, or condition substantially preventing the appearance of clinical symptoms of a disease, disorder or condition, up to and including returning the diseased entity to its condition prior to the development of the disease. Generally, the effectiveness of treatment is determined by comparing treated groups with non-treated groups.

The addition of a therapeutically effective amount of the one or more disclosed compounds encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A dosing regimen including the regularity of and mode of administration will be dependent on any of a number of factors including but not limited to the subject being treated; the severity of the condition; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Regardless of the route of administration, the therapeutic agent can be typically administered at a daily dosage of 0.01 mg to 30 mg/kg of body weight of subject receiving the treatment (e.g., 1 mg/kg to 5 mg/kg). The pharmaceutical formulation can be administered in multiple doses per day, if desired, to achieve the therapeutic effect and/or the total desired daily dose.

Pharmaceutical compositions that include the one or more disclosed compounds may be administered prior to, concurrently with, or after administration of additional or second pharmaceutical compositions that may or may not include the one or more disclosed compounds. Concurrent administration refers to pharmaceutical compositions that may be administered within about one minute of each other. If not administered concurrently, the additional or second pharmaceutical compositions may be administered a period of one or more minutes, hours, days, weeks, or months before or after the pharmaceutical composition that includes the one or more disclosed compounds. Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration. Cycling therapy may be used, for example, to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more unit dosages of the one or more disclosed compounds. The unit dosage would be enclosed in a preferably sterile container and would be comprised of the one or more disclosed compounds and a pharmaceutically acceptable carrier. In another aspect, the unit dosage would comprise one or more lyophilates of the one or more disclosed compounds. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the one or more disclosed compounds. Examples of such devices include, but are not limited to, a syringe, a drip bag, a patch or an enema. In some aspects of the invention, the device comprises the container that encloses the unit dosage. In another aspect, the kit may include one or more additional compounds for administration and administration instructions therefor.

Pharmaceutical compositions including the one or more disclosed compounds may be used in methods of treating a subject with coccidioidomycosis. Such methods involve the administration of an effective amount of a pharmaceutical composition that includes the one or more disclosed compounds and/or a pharmaceutically acceptable salt thereof to a subject with coccidioidomycosis (e.g., a mammal, such as a human or companion animal).

As used herein, subject refers to any organism that is capable of being infected with a pathogen, such as a fungal pathogen. For example, subject may refer to a human or a non-human animal. In some aspects, the non-human animal may be a companion animal, such as a dog, cat, or horse. In other aspects, the non-human animal may refer to livestock, murine animals, rabbits, etc.

EXAMPLES

Materials and Methods

High-Throughput LOPAC Library Screening Assay

In the experiments described below, *Coccidioides posadasii* Δcts2/Δard1/Δcts3 was used for assessing fungal response to a series of pharmaceutically active compounds. In brief, *C. posadasii* Δ*cts*2/Δard1/Δcts3 was grown under biosafety level two conditions for five days to ensure robustness of the culture for assay. The cultures were grown in conventional *Coccidioides* media: Glucose/Yeast Extract broth (GYE) growth medium that contains 10 g/L and 5 g/L yeast extract in addition to 50 μg/mL Hygromycin B. *C. posadasii* were allowed to grow to a sufficient concentration such that visible segmented mycelia and arthroconidia growth occurred in the medium, along with detectable turbidity. Thereafter, the cultures were filtered using a folded miracloth to enrich for arthroconidia. One milliliter of the filtered cultures was added to 100 mL of fresh GYE growth media and placed into an orbital bacterial incubator at 30° C. (rotation at 190 revolutions per minute). The cultures were allowed to grow for approximately 5-6 days. Once sufficient growth had occurred, the cultures were diluted 1:1 with fresh GYE medium and 40 μL of diluted culture were dispensed into clear 384-well microplates using a Multidrop™ liquid dispenser from ThermoFisher Scientific®. Specifically, the first two columns of each of the 384-well microplates used in the experiments contained media only as negative controls.

Once cultures were dispensed into the 384-well microplates, compounds were added to each of the wells. In particular, compounds contained in the LOPAC compound library (containing 1,280 known compounds) were used for this high-throughput screening assay. In this case, individual compounds were added to the cultures using an ATS-100 acoustic transfer system from EDC Biosystems. The wells of the microplates were dosed with 10 mM concentration stocks of the compounds of the LOPAC library to provide the desired final concentrations or the equivalent volume of DMSO, the vehicle control. Experiments were run in which the final concentration of the respective LOPAC library compounds was 5 μM (20 nL of stock compound solution) and 1 μM (4 nL of stock compound solution), with these concentrations being added to different microplates. Optical density readings at 600 nm (OD600) were taken immediately after the addition of the LOPAC library compounds and repeated every 24 hours for a total of 120 hours. The OD600 values were used to assess fungal growth over the course of the experiment. The experiment was repeated twice. In addition, staurosporine was used as a positive control.

In making determinations regarding which compounds in the LOPAC library inhibited growth, an analysis of the OD600 was performed. In particular, fungal growth that was inhibited by greater than 50%, relative to untreated vehicle-only controls (containing only DMSO), at any time point over the course of the experiment was counted as a positive "hit." In other words, the compounds that were considered to be hits exerted a negative effect on fungal growth that amounted to at least 50% growth inhibition compared to non-treated, DMSO-only controls.

Dose-Response Curves

In order to determine the $IC_{50}$ values of at least some of the positive hits from the high throughput assay described above, compounds of interest were first prepared to a stock concentration of 20 mM in DMSO, and then further serial diluted three-fold in DMSO to produce another 11 concentrations. The various compound stocks, ranging between 20 mM to 11.3 μM, were then transferred into Aurora source plates. DMSO was added to the remaining wells of the Aurora source plate as a vehicle control. Using the ATS-100, the serially diluted compound stocks and DMSO were added (100 nL) to untreated *Coccidioides* wells in a 'one-to-one' manner (well A1 of Aurora source plate to well A1 of untreated *Coccidioides* assay plate), producing an effective test concentration range of 50 μM to 28 nM of each compound. A final DMSO concentration of 0.25% is also maintained throughout the assay plate, eliminating the possibility of measuring toxicity produced by the DMSO itself. Similar to the screen, optical density readings at 600 nm (OD600) were taken immediately after the addition of the various compound concentrations and repeated every 24 hours for a total of 168 hours. By analyzing the fungal growth over the course of the experiment using the OD600 values, the relative potency of the compounds of interest can be assessed and ranked. The experiment was repeated multiple times.

Results

Run #1

As discussed above, the high throughput assay was repeated twice. The following section describes the results from the first run. In order to be assured of valid results, quality control measures were assessed for the control plates (i.e., no compound added) included in Run 1. Referring to FIGS. 1A and 1B, the growth over time values, as measured by the OD600, of the untreated *Coccidioides* wells shows that growth in the upper and lower portions of the microplates was very comparable, which indicates that edge effects on the plates were likely avoided. Moreover, the data in these figures also shows no change in the OD600 of the media-only wells (i.e., no growth over the course of the experiment), which suggests no contamination by other microorganisms. Moreover, as illustrated in FIG. 1B, the 48-hour data point is the first time point where there is significant growth (as measured by OD600), compared to media-only controls, in addition to acceptable Z-Factor scores. In addition, the fold change in the OD600 signal continues to improve over the course of the experiment, with improving Z-Factor scores, which indicates a robust and sensitive assay. In addition, the error bars and % CV are in a desirable range.

FIGS. 2A, 2B, 3A, and 3B illustrate quality control data for the microplates with added LOPAC library compounds. Similar to the data from the control plates of FIGS. 1A and 1B, control cultures from the 5 μM (FIGS. 2A and 2B) and 1 μM (FIGS. 3A and 3B) LOPAC library compound plates exhibited significant growth over the course of the 120 hour experiment. Moreover, at 48 hours in both sets of conditions, fungal growth was noticeable compared to the media-only/blank wells. In addition, the Z-Factor values at 48 hours started to rise to an acceptable range, with desirable Z-Factor values starting to appear at the 72 hour time point.

As a result of the experiments conducted in Run 1, the following compounds from the LOPAC library were identified as positive hits. As described above, a compound is considered a positive hit if, at either 5 μM or 1 μM, the compound inhibited fungal growth by greater than 50%, relative to the DMSO-only control. The following compounds were determined to be positive hits:

TABLE 2

| Compound Name |
|---|
| AC-93253 iodide |
| AS 604850 |
| Auranofin |
| Bay 11-7082 |
| Bay 11-7085 |
| beta-Lapachone |
| BIO |
| Calcimycin |
| Calmidazolium chloride |
| CGP 57380 |
| Chelerythrine chloride |
| Clotrimazole |
| Cyclosporin A |
| Dequalinium chloride hydrate |
| Eliprodil |
| Ellipticine |
| Fluphenazine dihydrochloride |
| GBR-12909 dihydrochloride |
| GBR-12935 dihydrochloride |
| IMS2186 |
| Indirubin-3'-oxime |
| Ketoconazole |
| Niclosamide |
| Nocodazole |
| PD-166285 hydrate |
| PD173952 |
| Pentamidine isethionate |
| Rotenone |
| Sanguinarine chloride |
| Sertraline hydrochloride |
| SR 59230A oxalate |
| Stattic |
| SU 5416 |
| Tamoxifen |
| Tamoxifen citrate |
| Trifluoperazine dihydrochloride |
| Triflupromazine hydrochloride |
| Tyrphostin A9 |
| Tyrphostin AG 879 |
| U-73343 |
| Voriconazole |
| ZM 39923 hydrochloride |

Figure 4:
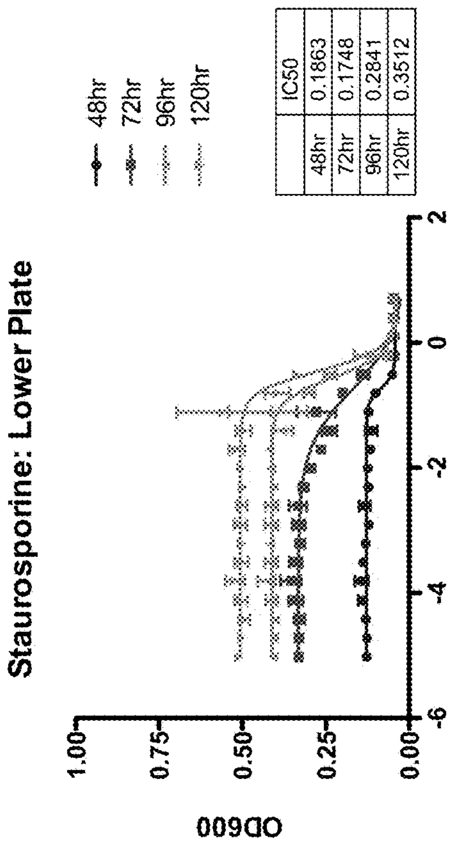
FIG. 4 depicts $IC_{50}$ data from positive controls used in assessing the LOPAC library. The graphs represent $IC_{50}$ values for *Coccidioides posadasii* that have been treated with varying concentrations of staurosporine and allowed to grow for 120 hours. The graphs depict data from samples located on the upper portion and lower portion of the 384-well microplate.
Figure 4:
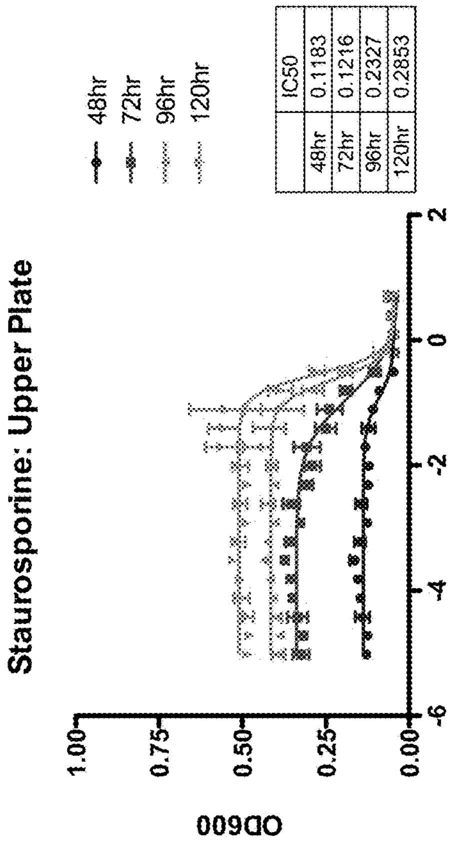

In addition, as a further control, a serial dilution of staurosporine was used as a positive control. Staurosporine is a known, potent anti-fungal compound. Referring now to FIG. 4, an analysis was conducted of the $IC_{50}$ values of staurosporine in the upper area and lower area of the microplates. In brief, the $IC_{50}$ values of staurosporine remained generally consistent over the course of the 120 hour experiment.

Run #2

Figures 5A, 5B:
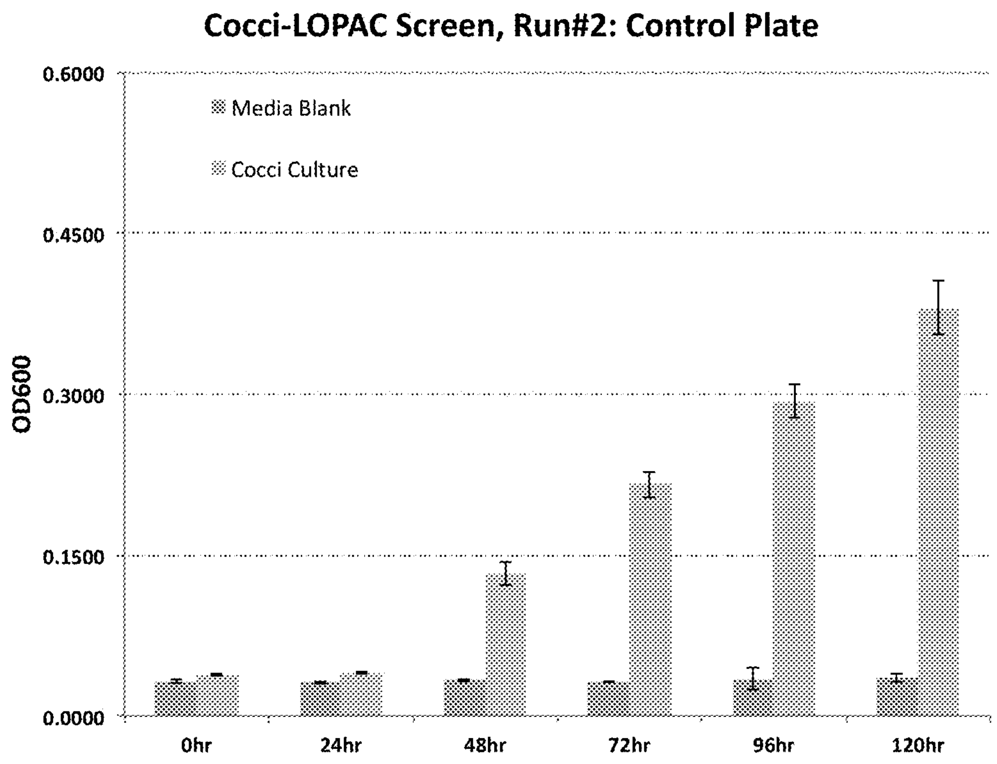
FIGS. 5A and 5B depict the results from a quality control plate illustrating the growth of *Coccidioides posadasii* over the course of a 120 hour experiment.
Figure 6A:
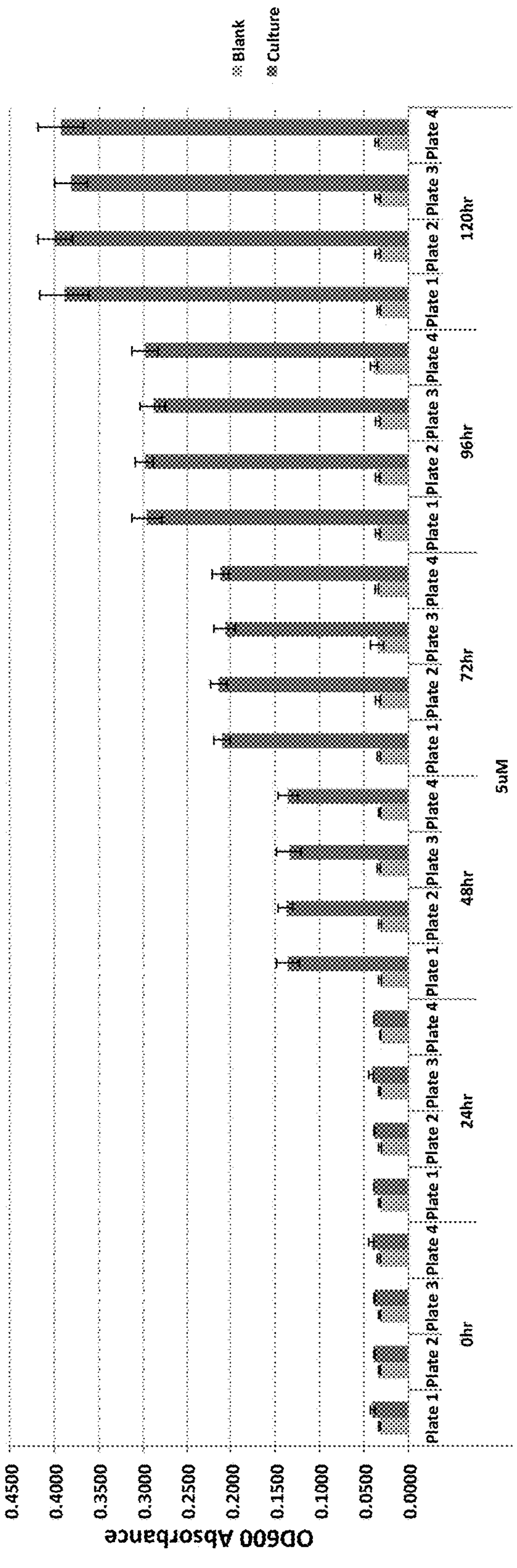
FIGS. 6A and 6B depict data from control samples from a series of microplates run with a 5 μM final concentration of compounds from the LOPAC library.
Figure 6B:
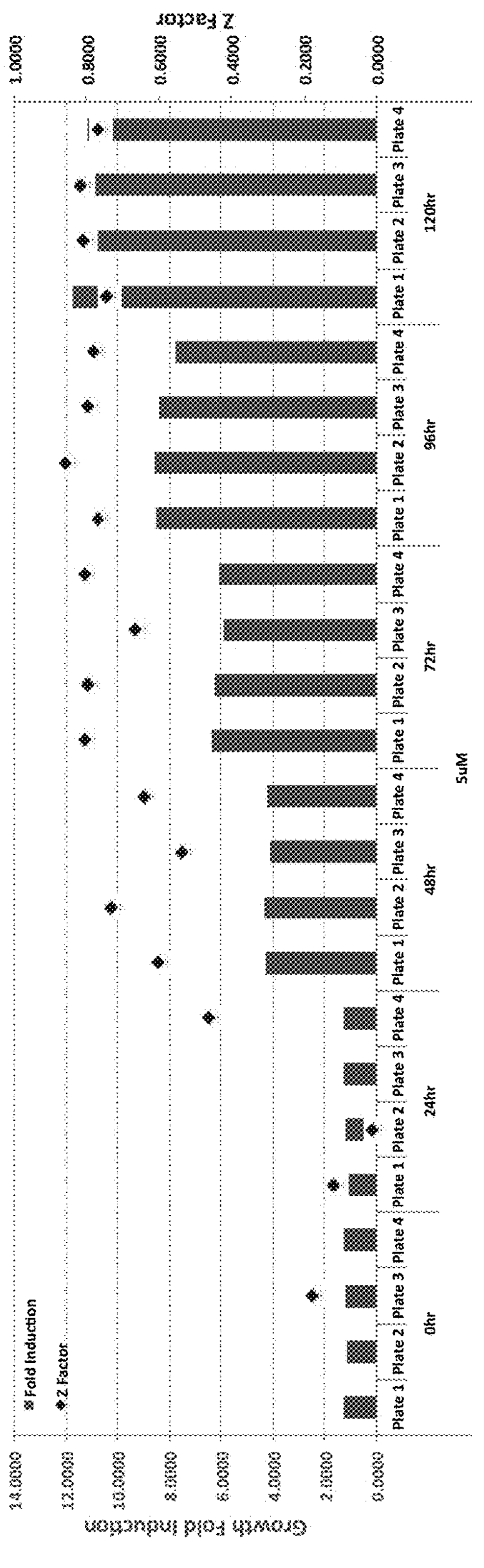
Figure 7A:
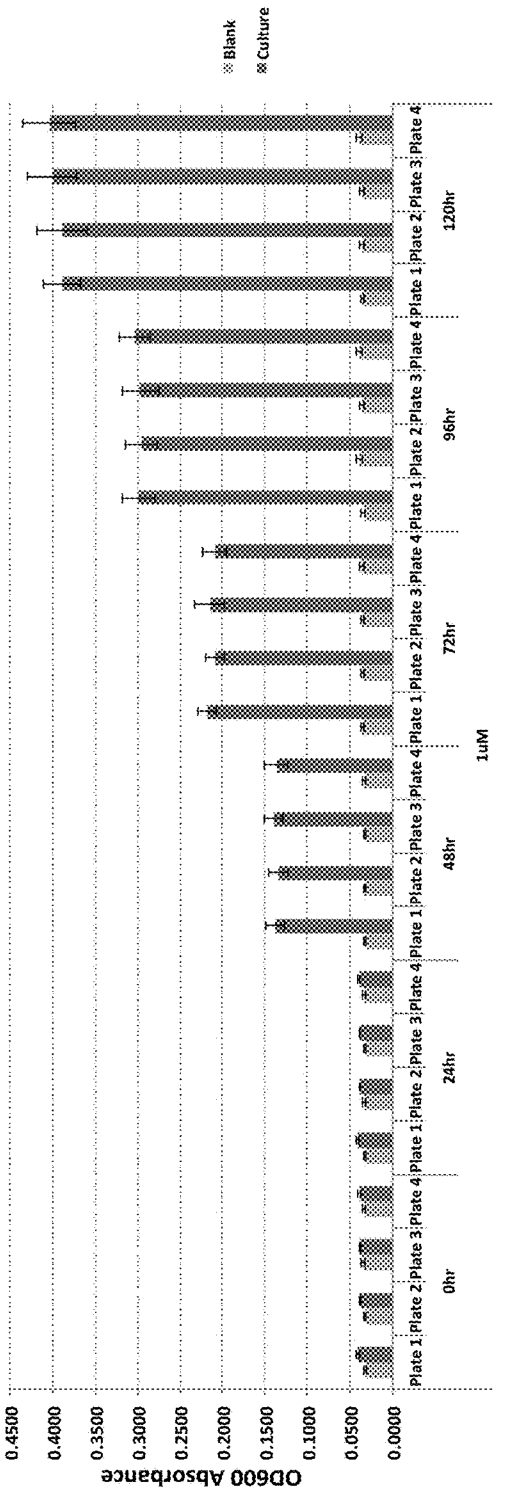
FIGS. 7A and 7B depict data from control samples from a series of microplates run with a 1 μM final concentration of compounds from the LOPAC library.
Figure 7B:
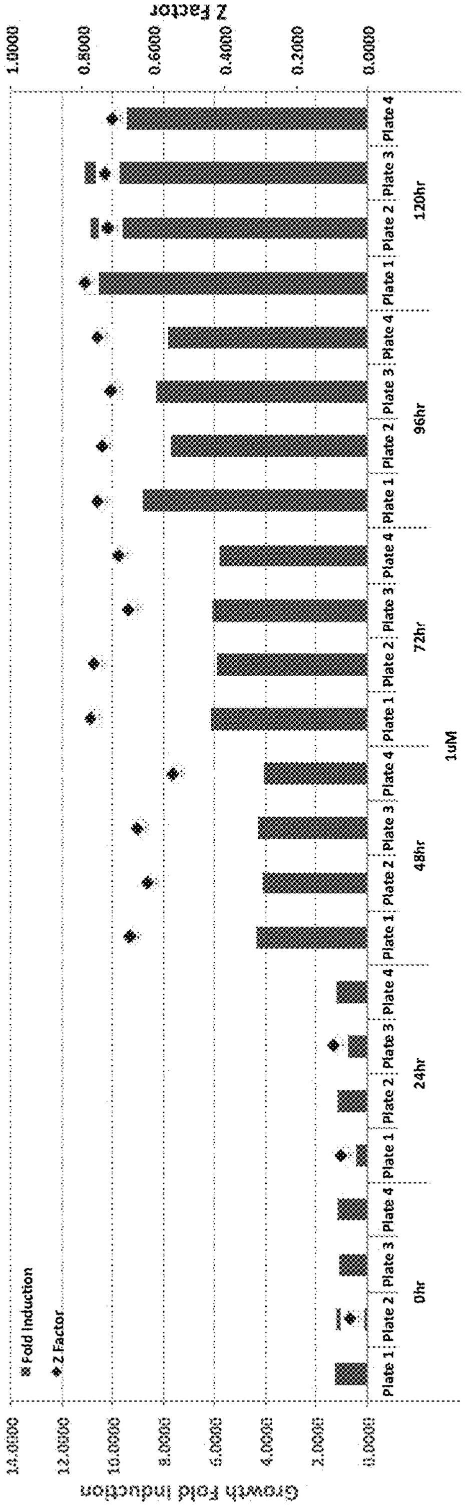

As discussed above, the high throughput assay was repeated and the results from Run 2 are described below. Once again, in order to be assured of valid results, quality control measures were assessed for the control plates (i.e., no compound added) included in Run 2. Referring to FIGS. 5A and 5B, the growth over time values, as measured by the OD600, of the untreated *Coccidioides* wells shows that growth in the upper and lower portions of the microplates was very comparable, which indicates that edge effects on the plates were likely avoided, similar to Run 1. Moreover, the data in these figures also shows no change in the OD600 of the media-only wells (i.e., no growth over the course of the experiment). Moreover, as illustrated in FIG. 5B, the 48-hour data point is the first time point where there is significant growth (as measured by OD600), compared to media-only controls, in addition to acceptable Z-Factor scores. In addition, the fold change in the OD600 signal continues to improve over the course of the experiment, with improving Z-Factor scores, which indicates a robust and sensitive assay. In addition, the error bars and % CV are in a desirable range.

FIGS. 6A, 6B, 7A, and 7B illustrate quality control data for the microplates with added LOPAC library compounds. Similar to the data from the control plates of FIGS. 5A and 5B, control cultures from the 5 μM (FIGS. 6A and 6B) and 1 μM (FIGS. 7A and 7B) exhibited significant growth over the course of the 120-hour experiment. Moreover, at 48 hours in both sets of conditions, fungal growth was noticeable compared to the media-only/blank wells. In addition, the Z-Factor values at 48 hours started to rise to an acceptable range, with desirable Z-Factor values starting to appear at the 72-hour time point.

As a result of the experiments conducted in Run 2, the following compounds from the LOPAC library were identified as positive hits. As described above, a compound is considered a positive hit if, at either 5 μM or 1 μM, the compound inhibited fungal growth by greater than 50%, relative to the DMSO-only control. The following compounds were determined to be positive hits:

TABLE 3

| Compound Name |
|---|
| (±)-Octoclothepin maleate |
| 1,3,5-tris(4-hydroxyphenyl)-4-propyl-1H-pyrazole |
| AC-93253 iodide |
| Artemether |
| AS 604850 |
| Auranofin |
| Bay 11-7085 |
| beta-Lapachone |
| BIO |
| Calcimycin |
| Calmidazolium chloride |
| CGP 57380 |
| CGS-12066A maleate |
| Chelerythrine chloride |
| Chlorpromazine hydrochloride |
| Chlorprothixene hydrochloride |
| cis-(Z)-Flupenthixol dihydrochloride |
| Clotrimazole |
| Cyclosporin A |
| Dequalinium chloride hydrate |
| Eliprodil |
| Ellipticine |
| GBR-12909 dihydrochloride |
| GBR-12935 dihydrochloride |
| Ifenprodil tartrate |
| IMS2186 |
| Indatraline hydrochloride |
| Indirubin-3'-oxime |
| JS-K |
| Ketoconazole |
| LP 12 hydrochloride hydrate |
| Methiothepin mesylate |
| ML-7 |
| Nocodazole |
| PD-166285 hydrate |
| PD173952 |
| Pentamidine isethionate |
| Prochlorperazine dimaleate |
| Quinacrine dihydrochloride |
| Ritanserin |
| Ruthenium red |
| Sanguinarine chloride |
| SCH 58261 |
| Sertraline hydrochloride |
| SR 59230A oxalate |
| SU 5416 |
| Tamoxifen |
| Tamoxifen citrate |
| TBBz |
| Thioridazine hydrochloride |
| Trifluoperazine dihydrochloride |
| Triflupromazine hydrochloride |
| Tyrphostin A9 |
| Voriconazole |
| Ziprasidone hydrochloride monohydrate |
| ZM 39923 hydrochloride |

Figure 8:
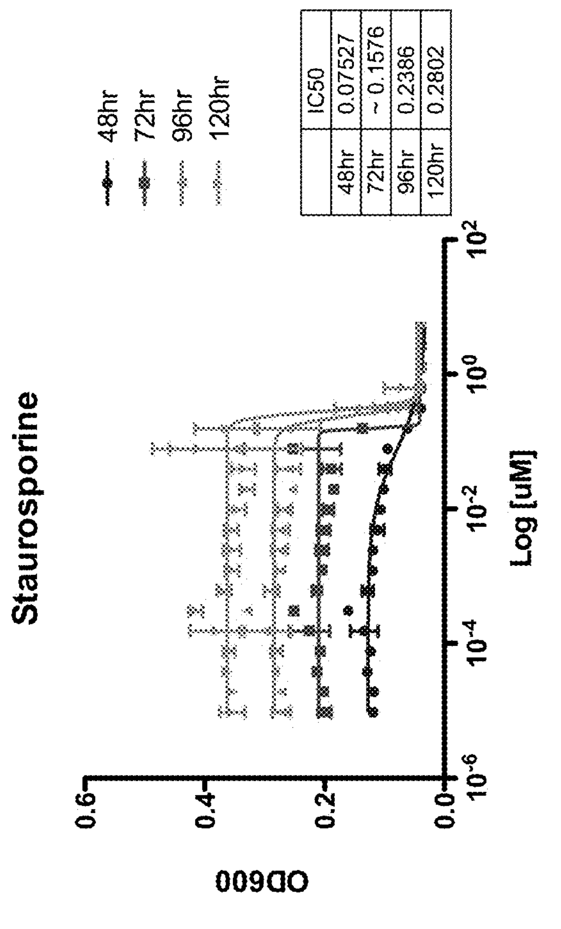
FIG. 8 depicts $IC_{50}$ data from positive controls used in assessing the LOPAC library. The graph represents $IC_{50}$ values for *Coccidioides posadasii* that have been treated with varying concentrations of staurosporine and incubated for 120 hours.

In addition, as a further control, a serial dilution of staurosporine was used as a positive control, similar to Run 1. Referring now to FIG. 8, an analysis was conducted of the $IC_{50}$ values of staurosporine. In brief, the $IC_{50}$ values of staurosporine remained generally consistent over the course of the 120 hour experiment, which is similar to the results obtained from Run 1. Overall, the compounds from the LOPAC library that exhibited the best inhibition of fungal growth (from both Runs 1 and 2) were detailed above in Table 1.

Figure 9:
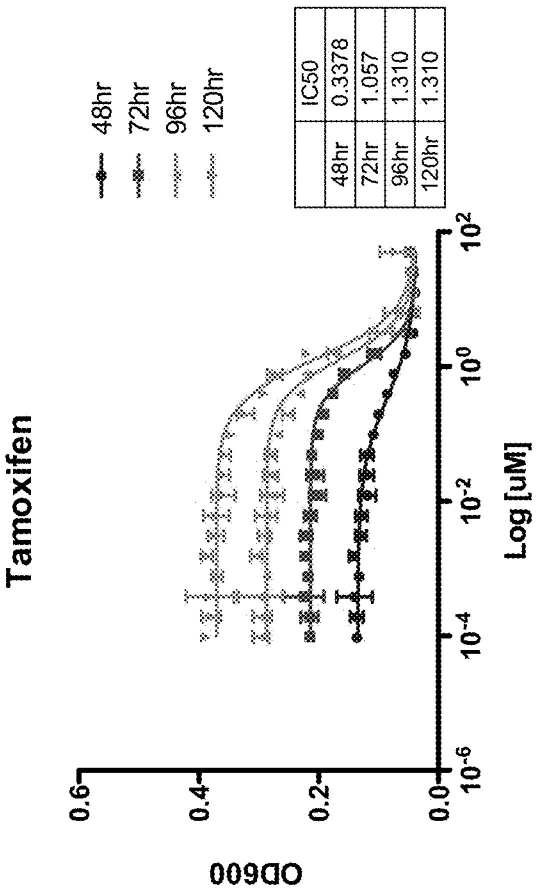
FIG. 9 depicts $IC_{50}$ data from *Coccidioides posadasii* that were treated with varying concentrations of tamoxifen and incubated for 120 hours.

Tamoxifen, a compound used in the treatment of early and advance breast cancer, infertility, gynecomastia, and bipolar disorder, was identified as a strong positive hit in Run 1. As such, a serial dilution of tamoxifen was run to determine the $IC_{50}$ values over the course of the 120 hour experiment. As illustrated in FIG. 9, the $IC_{50}$ values slowly increased over the course of the experiment, which was likely due to the continued growth of the fungus. However, tamoxifen still exhibited strong fungal growth inhibitory properties over the course of the experiment.

Referring now to FIG. 10, serial dilutions of multiple active pharmaceutical ingredients identified above were performed to determine the $IC_{50}$ values over the course of the 168 hour experiment. As illustrated in FIG. 10, the replicate experiments demonstrated that some of the tested compounds provide desirable $IC_{50}$ values (i.e., lower values) than other compounds.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method of treating a subject having an infection caused by *Coccidioides*, the method comprising the step of administering to the subject a therapeutically effective amount of a combination of fluconazole and a fungicidal or fungistatic agent selected from the group consisting of sertraline and tamoxifen.

2. The method of claim 1, wherein the subject is a mammal.

3. The method of claim 1, wherein the subject is one of a human and a companion animal.

4. The method of claim 3, wherein the companion animal is a canine.

5. The method of claim 1, wherein the *Coccidioides* is at least one of *Coccidioides immitis* or *Coccidioides* posadasii.

6. The method of claim 1, wherein the fungicidal agent or fungistatic agent and the fluconazole are administered sequentially.

7. The method of claim 1, wherein the fungicidal agent or fungistatic agent and the fluconazole are administered concurrently.

8. A method for treating a subject with Valley Fever, the method comprising the step of administering to the subject a therapeutically effective amount of a combination of fluconazole and a fungicidal agent or fungistatic agent selected from the group consisting of sertraline and tamoxifen.

9. The method of claim 8, wherein the subject is one of a human and a companion animal.

10. The method of claim 9, wherein the companion animal is a canine.

11. The method of claim 8, wherein the fungicidal agent or fungistatic agent and the fluconazole are administered sequentially.

12. The method of claim 8, wherein the subject is a mammal.

13. The method of claim 8, wherein the fungicidal agent or fungistatic agent and the fluconazole are administered concurrently.

14. A method of treating a subject having an infection caused by *Coccidioides*, the method comprising the step of administering to the subject a therapeutically effective amount of a combination of fluconazole and a hormone-inhibiting companion agent selected from the group consisting of sertraline and tamoxifen.

15. The method of claim 14, wherein the subject is a mammal.

16. The method of claim 14, wherein the subject is one of a human and a companion animal.

17. The method of claim 16, wherein the companion animal is a canine.

18. The method of claim 14, wherein the *Coccidioides* is at least one of *Coccidioides immitis* or *Coccidioides* posadasii.

19. The method of claim 14, wherein the hormone-inhibiting companion agent and the fluconazole are administered sequentially.

20. The method of claim 14, wherein the hormone-inhibiting companion agent and the fluconazole are administered concurrently.

* * * * *